United States Patent
Frerichs et al.

(10) Patent No.: US 10,737,048 B2
(45) Date of Patent: Aug. 11, 2020

(54) DEVICE FOR SUPPORTING A PATIENT INTERFACE ON THE USERS HEAD

(71) Applicant: Loewenstein Medical Technology S.A., Luxembourg (LU)

(72) Inventors: Arnold Frerichs, Buxtehude (DE); Joachim Gardein, Icod de los Vinos (ES)

(73) Assignee: LOWENSTEIN MEDICAL TECHNOLOGY S.A., Luxembourg (LU)

(*) Notice: Subject to any disclaimer, the term of this patent is extended or adjusted under 35 U.S.C. 154(b) by 684 days.

(21) Appl. No.: 15/346,838

(22) Filed: Nov. 9, 2016

(65) Prior Publication Data
US 2017/0136201 A1 May 18, 2017

(30) Foreign Application Priority Data
Nov. 12, 2015 (DE) .................... 20 2015 007 792 U (51) Int. Cl.
| | | |
|---|---|---|
| A61M 16/06 | (2006.01) | |
| F16F 1/373 | (2006.01) | |
| A61B 1/00 | (2006.01) | |
| A61M 16/08 | (2006.01) | |
| A61M 16/20 | (2006.01) | |

(52) U.S. Cl.
CPC ..... A61M 16/0633 (2014.02); A61B 1/00154 (2013.01); A61M 16/06 (2013.01); A61M 16/0683 (2013.01); A61M 16/08 (2013.01); A61M 16/208 (2013.01); F16F 1/373 (2013.01)

(58) Field of Classification Search
CPC .......... A61M 16/0633; A61M 16/0683; A61M 16/208; A61M 16/08; A61M 16/06; A61M 16/0622; A61B 1/00154; F16F 1/373
See application file for complete search history.

(56) References Cited

U.S. PATENT DOCUMENTS

| | | | | |
|---|---|---|---|---|
| 5,174,049 | A * | 12/1992 | Flemming | A43B 1/0009 36/28 |
| 6,679,261 | B2 * | 1/2004 | Lithgow | A61M 16/06 128/205.25 |
| D807,497 | S * | 1/2018 | Kwok | D24/110.1 |
| 2004/0177850 | A1 * | 9/2004 | Gradon | A61M 16/06 128/206.21 |
| 2005/0011522 | A1 * | 1/2005 | Ho | A61M 16/06 128/206.21 |
| 2006/0130844 | A1 * | 6/2006 | Ho | A61M 16/06 128/206.24 |
| 2012/0012113 | A1 * | 1/2012 | Chien | A61M 16/06 128/206.21 |

* cited by examiner

*Primary Examiner* — Theodore J Stigell
(74) *Attorney, Agent, or Firm* — Abel Schillinger, LLP (57) ABSTRACT

Disclosed is a spring arrangement for elastically supporting a patient interface on a patient, wherein a spring body is provided, said spring body having a base structure, which is connected to the patient interface via connecting elements, wherein, starting from the base structure, inner walls and outer walls are arranged in an inclined state in relation to an axis extending in the spring direction, and wherein the walls, at least in part, form a honeycomb structure, and having a bearing surface, at least part of which extends parallel to the base structure, wherein the bearing surface is spaced apart from the base structure by at least two honeycomb structures.

24 Claims, 7 Drawing Sheets

DEVICE FOR SUPPORTING A PATIENT INTERFACE ON THE USERS HEAD

CROSS-REFERENCE TO RELATED APPLICATIONS

The present application claims priority under 35 U.S.C. § 119 of German Utility Model Application No. 20 2015 007 792, filed Nov. 12, 2015, the entire disclosure of which is expressly incorporated by reference herein.

BACKGROUND OF THE INVENTION

1. Field of the Invention

The invention relates to a device for supporting a patient interface on the user's head.

2. Discussion of Background Information

A patient interface (PI) is used to provide the patient with breathing gas supplied from a ventilator. Patient interfaces can be realized in different embodiments, for example in the form of nasal cannulas, nasal pillow masks, nasal masks or full-face masks The PI is connected to the ventilator typically via a breathing-gas tube and is fixed on the user's head.

A precise fit of the PI is necessary in order to avoid therapy being impaired as a result of slipping or loosening. Forehead supports are used to ensure reliable positioning and to reduce the forces which act on the face. Reliable positioning in the region of a patient's face, however, is only ensured by the additional use of an adjustable forehead support with a forehead pad on the PI. Undesirable detachment or slipping from the user's face and resulting leakages are avoided. Both the wearing comfort and the stability are increased by the use of an adjustable forehead support. These help to adapt the PI to the different physiognomies. The adjustment range thus typically has to be at least 10 mm. Such forehead supports have means for defining the height and/or the distance from the forehead. Many adjusting means are of multi-part construction and are therefore often complicated to adjust and difficult to clean. Direct adaptation while being worn is usually not possible. An additional component is constituted by an elastic forehead pad, which serves for resting against the forehead.

In view of the foregoing, it would be advantageous to have available a device of the type mentioned in the introduction such that functional, easy-to-use adjustment of the forehead support is provided and there is a high level of functionality and robustness along with a straightforward construction.

SUMMARY OF THE INVENTION

The present invention provides a spring arrangement for elastically supporting a patient interface on a patient, wherein a spring body is provided, said spring body having a base structure, which is connected to the patient interface via connecting means, wherein, starting from the base structure, inner walls and outer walls are arranged in an inclined state in relation to an axis extending in the spring direction, and wherein the walls, at least in part, form a honeycomb structure, and having a bearing surface, at least part of which extends parallel to the base structure, wherein the bearing surface is spaced apart from the base structure by at least two honeycomb structures.

The present invention also provides a patient interface (20) with a spring arrangement (1) for elastically supporting the patient interface on a patient, wherein the patient interface (20) comprises a forehead support (21) and a forehead pad, which may be designed in the form of a spring arrangement (1), wherein the patient interface comprises four retaining elements (22) or strap clips for strap ends of a head-strap arrangement, and wherein the patient interface comprises an interchangeable angled connection (23), via which the patient interface is connected to the breathing tube, and wherein at least three different angled connections (23a, b, c) can he adapted to the patient interface (20), wherein a spring body (1) is provided, said spring body having a base structure (2), which is connected to the patient interface via connecting elements (3), wherein, starting from the base structure (2), walls (4, 14) are arranged in an inclined state in relation to an axis (11) extending in the spring direction, and having a bearing surface (10), at least part of which extends parallel to the base structure (2), wherein the bearing surface (10) is spaced apart from the base structure (2) by at least two walls.

The present invention further provides a patient interface (20) with a spring arrangement (1) for elastically supporting the patient interface on a patient, wherein the patient interface (20) comprises a forehead support (21) and a forehead pad, which may be designed in the form of a spring arrangement (1), wherein the patient interface comprises four retaining elements (22) or strap clips for strap ends of a head-strap arrangement, and wherein the patient interface comprises an interchangeable angled connection (23), via which the patient interface is connected to the breathing tube, and wherein at least three different angled connections (23a, b, c) can be adapted to the patient interface (20), wherein, between the securing ring and the body of the patient interface or in the angled connection, the vented angled connection (24a) has exhalation ports (25) via which breathing gas can be flushed out continuously, and the non-vented angled connection (24b) has no exhalation ports via which breathing gas is flushed out continuously, wherein an additional safeguard in the event of the apparatus failing is provided by an anti-asphyxia valve (AAV) (26) in the non-vented angled connection (24b), and the non-vented angled connection (24b), for this purpose, has an atmospheric-air port, at least part of which can be closed from the inside by a membrane, wherein the membrane is inserted into the angled connection such that the membrane closes the atmospheric-air port during normal therapy operation by the therapy pressure applied and, in the event of a drop in pressure, the membrane swings back into its starting position and frees the atmospheric-air port, and the angled connection (24c) is designed in the form of an endoscope adapter (24c) and allows for a bronchoscopy to be carried out without the patient's breathing having to be interrupted, wherein the angled connection has a reclosable opening (30) for the endoscope, it being possible for said opening to be closed by a closure cap (31), wherein the opening is dimensioned such that conventional endoscopes can be readily inserted, wherein the opening essentially abuts the endoscope, and therefore leakages are reduced, wherein a spring body (1) is provided, said spring body having a base structure (2), which is connected to the patient interface via connecting means (3), wherein, starting from the base structure (2), walls (4, 14) are arranged in an inclined state in relation to an axis (11) extending in the spring direction, and having a bearing surface (10), at least part of which extends parallel to the base structure (2), wherein the bearing surface (10) is spaced apart from the base structure (2) by at least two walls.

In one aspect of the spring arrangement, the outer walls of the spring body may form at least one knee.

In another aspect of the spring arrangement, the knee may be oriented radially outward.

In another aspect of the spring arrangement, the outer walls of the spring body may form at least two knees, of which one knee is oriented radially outward and one knee is oriented inward.

In another aspect of the spring arrangement, the walls are capable of being collapsed elastically in each case at the knee.

In another aspect of the spring arrangement, the walls and/or the honeycombs may terminate at a central structure, as seen in the spring direction, with a contact location.

In another aspect of the spring arrangement, the wall thickness of the contact location may be reduced.

In another aspect of the spring arrangement, from the central structure, inner walls and outer walls may extend in an inclined state in relation to the spring direction and open out, by way of at least one contact location, in a bearing surface, at least part of which extends parallel to the base structure.

In another aspect of the spring arrangement, at least part of the bearing surface may extend parallel to the base structure and parallel to the central structure.

In another aspect of the spring arrangement, the walls together with the bearing surface may form at least one honeycomb structure.

In another aspect of the spring arrangement, the wall thicknesses may be from about 1.2 mm to about 3.2 mm.

In another aspect of the spring arrangement, the wall thicknesses may be about 2.2 mm, In another aspect of the spring arrangement, the wall thickness of at least one contact location may be thinner than that of the walls.

In another aspect of the spring arrangement, the thickness of the walls and/or the material thickness of the honeycomb structure and/or the geometry of the honeycomb structure may vary in the spring direction.

In another aspect of the spring arrangement, the spring displacement over the first stage may be about 6 mm.

In another aspect of the spring arrangement, the spring displacement over the second stage may be about 5 mm.

In another aspect of the spring arrangement, the spring constant overall may range from about 0.26 to about 0.46.

In another aspect of the spring arrangement, the spring constant overall may be 0.36+/−10%.

In another aspect of the spring arrangement, the spring constant over the first stage may range from 0.18-0.32+/−10%.

In another aspect of the spring arrangement, the spring constant over the second stage may range from 0.36-0.50+/−10%.

In another aspect of the spring arrangement, the force-displacement relationship of the spring arrangement may not be linear and may have a progressive behavior in which the spring force increases over-proportionately in relation to the displacement.

In another aspect of the spring arrangement, the force-displacement relationship over the first stage of the spring arrangement may be approximately linear.

In another aspect of the spring arrangement, the spring body may be formed from preferably soft/resilient plastics material.

In another aspect of the spring arrangement, the spring body may be designed in the form of a single-piece molding.

In another aspect of the spring arrangement, the spring body may be formed from LSR.

In another aspect of the spring arrangement, the spring body may have a Shore hardness ranging from about 35-66 Shore A.

In another aspect of the spring arrangement, the spring body may have a Shore hardness of 40 Shore A+/−10%.

In another aspect of the spring arrangement, the spring body may have a Shore hardness of 60 Shore A+/−10%.

BRIEF DESCRIPTION OF THE DRAWINGS

Further advantages and features of the present invention result from the description of the exemplary embodiments, which are explained hereafter with reference to the appended drawings.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
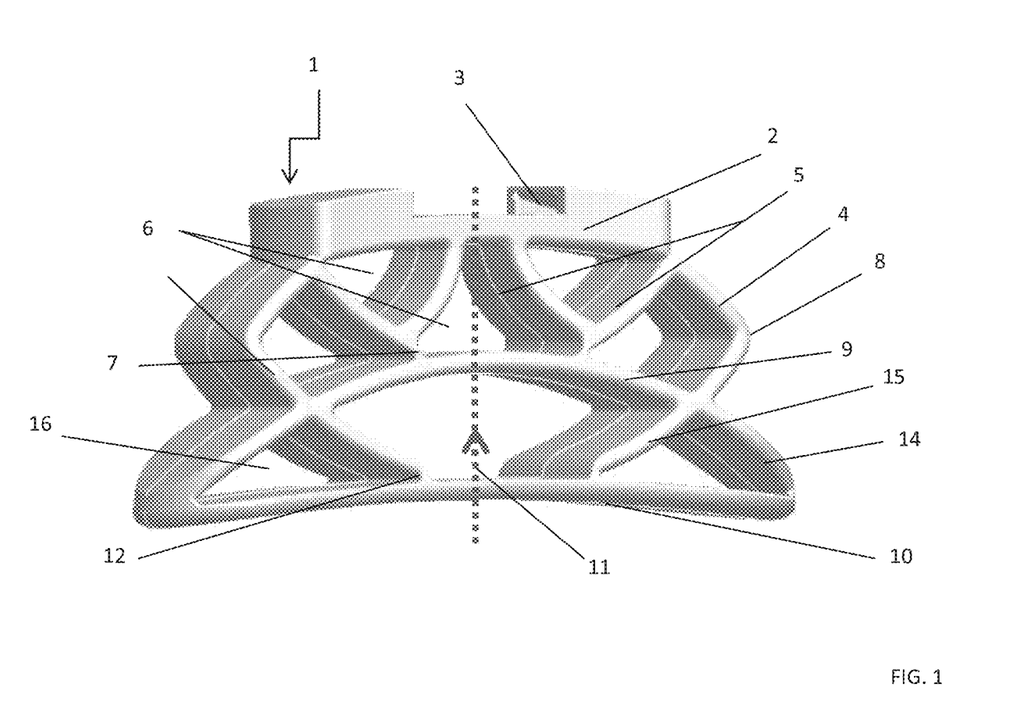
FIG. 1 shows a spring arrangement according to the invention for elastically supporting a patient interface on a patient.

FIG. 1 shows a spring arrangement for elastically supporting a patient interface on a patient, wherein a spring body (1) is provided, said spring body having a base structure (2), which is connected to the patient interface (not shown) via connecting means (3). For example, the forehead support of the PI has complementary connecting means which assist straightforward mechanical connection. As an alternative, the spring arrangement may be fixed to the forehead support of the PI via the connecting means (3), for example using 2-component technology. Starting from the base structure (2), inner walls (5) and outer walls (4) are arranged in an inclined state in relation to an axis (11) extending in the spring direction, and wherein the walls (2, 4, 5), at least in part, form a honeycomb structure (6), and the spring body also has a bearing surface (10), at least part of which extends parallel to the base structure (2), wherein the bearing surface (10) is spaced apart from the base structure (2) by at least two honeycomb structures (6, 16). The spring arrangement additionally has outer walls (4, 5) of the spring body (1), and these outer walls form at least one knee (8) which is oriented radially outward. The walls can preferably be collapsed elastically in each case at the knee (8). The walls (4, 5) and/or the honeycombs (6) terminate at a central structure (9), as seen in the spring direction (11), with a contact location (7). The wall thickness of the contact location (7) is thinner than that of the walls (2, 4, 5). From the central structure (9), inner walls (15) and outer walls (14) extend in an inclined state in relation to the spring direction (11). These walls (14, 15) open out, by way of at least one contact location (12), in a bearing surface (10), at least part of which extends parallel to the base structure (2). At least part of the bearing surface (10) extends parallel to the base structure (2) and parallel to the central structure (9), said bearing surface serving to come into contact with the patient, for example on the forehead. The walls (14, 15) together with the bearing surface (10) form at least one honeycomb structure (16). This honeycomb structure (16) is, for example, triangular. The wall thicknesses are 1.2-3.2 mm. The wall thicknesses are preferably 1.8-2.7 mm. The wall thickness of the bearing surface (10) is, for example, thicker than that of the walls (4, 5, 14, 15). The wall thickness of the bearing surface (10) is, for example, 2.5 mm+/−10%. The thickness of the walls (4, 5, 14, 15) is, for example, 2.2 mm+/−10%. The wall thickness of the contact location (7) is thinner than that of the walls (4, 5, 14, 15). The wall thickness of the contact location (12) is thinner than that of the walls (4, 5, 14, 15).

The thickness of the walls and/or the material thickness of the honeycomb structure and/or the geometry of the honeycomb structure and/or the material vary/varies in the spring direction (11).

The spring arrangement is formed from soft/resilient plastics material, for example from LSR (Liquid Silicone Rubber). The spring arrangement is designed preferably in the form of a single-piece molding.

The spring arrangement is distinguished by a Shore hardness ranging from 35-66 Shore A. The spring arrangement made of LSR has a honeycomb structure which compresses under pressure.

The Shore hardness is alternatively 40 Shore A+/−10%. The Shore hardness may also be 60 Shore A+/−10%.

The honeycomb or wall structure is tapered specifically at 4 positions (7, 12), and therefore the spring arrangement can be pushed in more easily and uniformly here under pressure.

Figure 2:
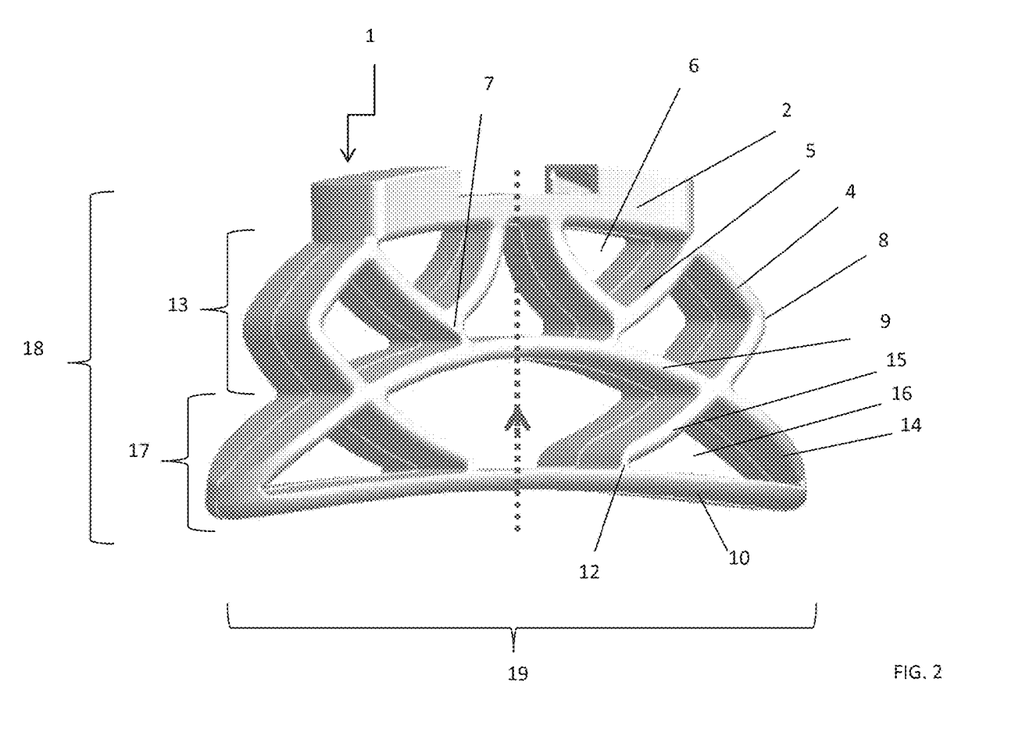
FIG. 2 shows another spring arrangement according to the invention for elastically supporting a patient interface on a patient.

FIG. 2 shows a spring arrangement for elastically supporting a patient interface on a patient, wherein a spring body (1) is provided, said spring body having a base structure (2), which is connected to the patient interface (not shown) via connecting means (3). For example, the forehead support of the PI has complementary connecting means which assist straightforward mechanical connection. As an alternative, the spring arrangement may be fixed to the forehead support of the PI via the connecting means (3), for example using 2-component technology. Starting from the base structure (2), inner walls (5) and outer walls (4) are arranged in an inclined state in relation to an axis (11) extending in the spring direction, and wherein the walls (2, 4, 5), at least in part, form a honeycomb structure (6), and the spring body also has a bearing surface (10), at least part of which extends parallel to the base structure (2), wherein the bearing surface (10) is spaced apart from the base structure (20) by at least two honeycomb structures (6, 16). The spring arrangement additionally has outer walls (4, 5) of the spring body (1), and these outer walls form at least one knee (8) which is oriented radially outward. The walls can preferably be collapsed elastically in each case at the knee (8). The walls (4, 5) and/or the honeycombs (6) terminate at a central structure (9), as seen in the spring direction (A), with a contact location (7). The wall thickness of the contact location (7) is thinner than that of the walls (2, 4, 5). From the central structure (9), inner walls (15) and outer walls (14) extend in an inclined state in relation to the spring direction (11). These walls (14, 15) open out, by way of at least one contact location (12), in a bearing surface (10), at least part of which extends parallel to the base structure (2). At least part of the bearing surface (10) extends parallel to the base structure (2) and parallel to the central structure (9), said bearing surface serving to come into contact with the patient, for example on the forehead. The walls (14, 15) together with the bearing surface (10) form at least one honeycomb structure (16). This honeycomb structure (16) is, for example, triangular. The wall thicknesses are about 1.2-3.2 mm. The wall thicknesses are preferably about 1.8-2.7 mm. The wall thickness of the bearing surface (10) is, for example, thicker than that of the walls (4, 5, 14, 15). The wall thickness of the bearing surface (10) is, for example, about 2.5 mm+/−10%. The thickness of the walls (4, 5, 14, 15) is, for example, about 2.2 mm+/−10%. The wall thickness of the contact location (7) is thinner than that of the walls (4, 5, 14, 15). The wall thickness of the contact location (12) is thinner than that of the walls (4, 5, 14, 15). The thickness of the walls and/or the material thickness of the honeycomb structure and/or the geometry of the honeycomb structure and/or the material vary/varies in the spring direction (11). The spring arrangement is formed from soft/resilient plastics material, for example from LSR. The spring arrangement is designed preferably in the form of a single-piece molding. The spring arrangement is distinguished by a Shore hardness ranging from about 35 to about 66 Shore A. The spring arrangement made of LSR. (Liquid Silicone Rubber) has a honeycomb structure which compresses under pressure. The Shore hardness is alternatively about 40 Shore A+/−10%. The Shore hardness may also be about 60 Shore A+/−10%. The honeycomb or wall structure is tapered specifically at 4 positions (7, 12), and therefore the spring arrangement can be pushed in more easily and uniformly here under pressure.

The spring arrangement has a first spring displacement (17) between the bearing surface (10) and the central structure (9), wherein the walls (14, 15) and (10) form at least two honeycombs (16), which are for example triangular. Pressure applied in the spring direction (11) compresses the honeycombs (16) such that, under the action of force, the bearing surface (10) and the central structure (9) move toward one another. The spring displacement over the first stage (17) is from about 3 to about 8 mm, and is preferably about 6 mm+/−10%.

The spring arrangement has a second spring displacement (13) between the central structure (9) and the base (2), wherein the walls (4, 5) and (2) and also (9) form at least two honeycombs (6), which are for example triangular. Pressure applied in the spring direction (11) compresses the honeycombs (6) such that, under the action of force, the base (2) and the central structure (9) move toward one another. The spring displacement over the second stage (13) is from about 3.5 to about 7 mm, and is preferably about 5 mm+/−10%.

The spring arrangement has an overall spring constant ranging from about 0.26 to about 0.46 N/mm.

The spring constant overall is preferably about 0.36 N/mm+/−10%.

The spring constant over the first stage (17) ranges from 0.18-0.32+/−10%.

The spring constant over the second stage (13) ranges from 0.36-0.50+/−10%.

The force-displacement relationship of the spring arrangement is not linear and has a progressive behavior in which the spring force increases overproportionately in relation to the displacement. This applies, in particular, to the second stage (13). The force-displacement relationship over the first stage (17) of the spring arrangement is more or less linear. The height (18) is about 25-35 mm, preferably about 33 mm+/−10%. The width (19) is about 55-75 mm, preferably about 65 mm+/−10%.

Figure 3:
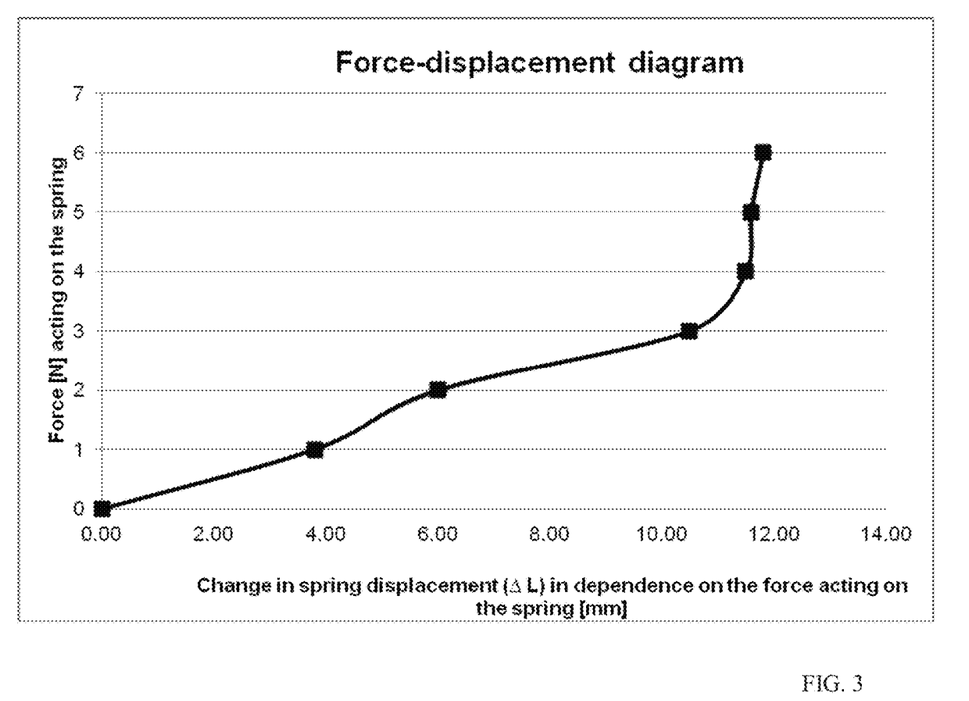
FIG. 3 shows a force-displacement diagram of the spring arrangement of FIG. 2.

FIG. 3 shows the force-displacement diagram of the spring arrangement. It can be seen here that the maximum spring displacement is 12 mm. In the range up to a spring displacement of 4 mm, at up to 1 N, the force-displacement relationship over the first stage of the spring arrangement is linear. For a spring displacement ranging from 4-6 mm, the force-displacement relationship of the spring arrangement is more or less linear. However, a force of likewise 1 N is necessary here for the change in displacement of 2 mm. The spring arrangement is already harder over this range. For a spring displacement ranging from 6-10 mm, the force-displacement relationship of the spring arrangement is linear. A force of 1 N is necessary here for the change in displacement of 4 mm. The spring arrangement is already softer again over this range. For a spring displacement ranging from 10-12 mm, the force-displacement relationship of the spring arrangement is progressive. A force of 2 N is necessary here for the change in displacement of 2 mm. The spring arrangement can also be configured according to the invention such that the force-displacement relationship of the spring arrangement is not linear, at least in part, and has a degressive behavior in which the spring force increases underproportionately in relation to the displacement.

Figure 4:
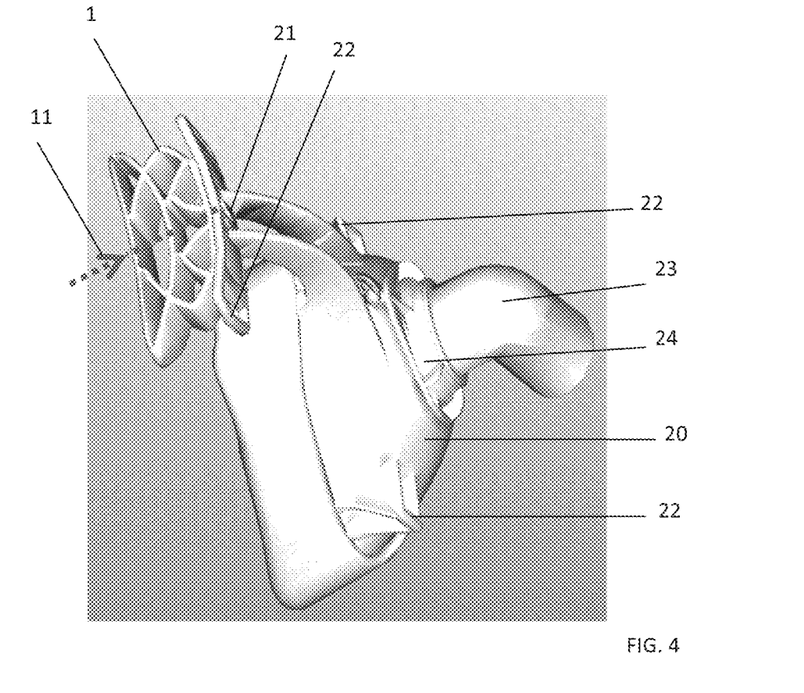
FIG. 4 shows a patient interface with a spring arrangement according to the invention.

FIG. 4 shows a patient interface with the spring arrangement (1). The patient interface (PI) has a mask body, on which the breathing-gas tube (not illustrated) is connected to the PI for example via a ball joint and a rotary sleeve. The mask body has, as sealing means relative to the patient's face, a sealing element in the form of a mask bead with a lip seal. Fixing in the region of a patient's head can take place via headgear or a head-strap arrangement. The strap ends of the headgear or of the head-strap arrangement are fastened in a releasable manner on the PI, on the one hand, via mounting devices in the cheek region and, on the other hand, via mounts in the forehead region. For this purpose, the strap ends are guided through the mounts and fixed on the strap arrangement via a hook-and-loop fastener. The mounts on the forehead support have a slot for the insertion of the strap arrangement. A mask-mounted supporting body with the spring arrangement (1) serves for supporting the patient interface in the region of the patient's forehead. The supporting body comprises crosspieces, which extend from the mask body, and a mount for the spring arrangement (1), said mount being located at the ends of the crosspieces.

The spring arrangement (1) is connected mechanically to the mount or alternatively, on a permanent basis, is adhesively bonded to the mount or injection-molded thereto using 2-component technology. The particular advantage of the spring arrangement (1) is the single-piece construction, which provides for, at the same time, automatic adjustment/setting and reliable positioning on the forehead. Automatic adjustment/setting of the spring arrangement (1) takes place depending on the tightening force of the head-strap arrangement. The tightening force of the strap arrangement results in the spring arrangement (1) compressing to a more or less pronounced extent and thus always providing for the spacing or distance of the patient interface which is optimum for the specific patient. Even if the patient changes position while asleep, the spring arrangement (1) compensates for the change again.

Figure 5:
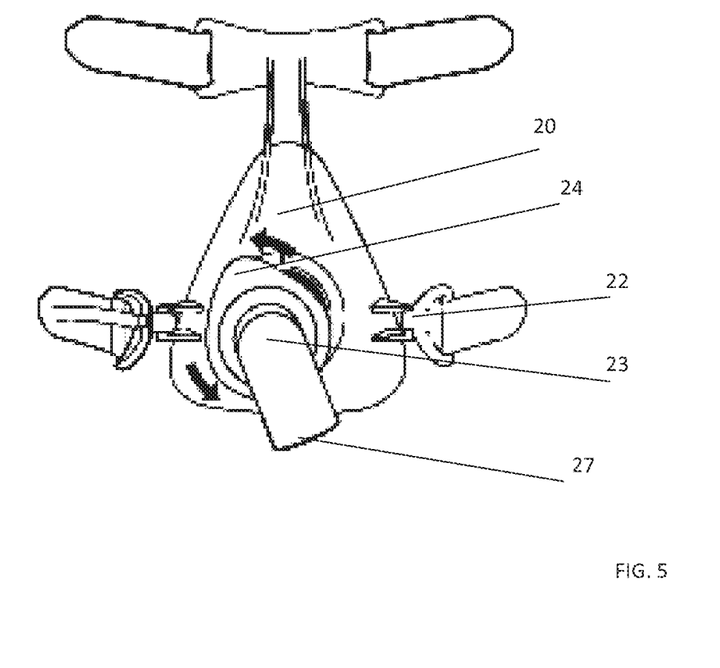
FIG. 5 shows a patient interface with an angled connection via which the patient interface is connected to a breathing tube.

In FIG. 5: the patient interface has an angled connection (23a, b, c), via which the patient interface is connected to the breathing tube. The angled connection is mounted in a rotatable manner in the patient interface. The angled connection can preferably be rotated through 360°. For example, the angled connection may be designed in the form of a ball joint. Along its extent which is directed away from the patient interface, the angled connection has a cone (27) which serves for connecting to the breathing tube.

The angled connection is connected to the body of the patient interface in a releasable manner for example via a securing ring (29). The securing ring with the angled connection releases from the mask body for example by way of a lever/rotary movement or of a rotary movement.

Figure 6A:
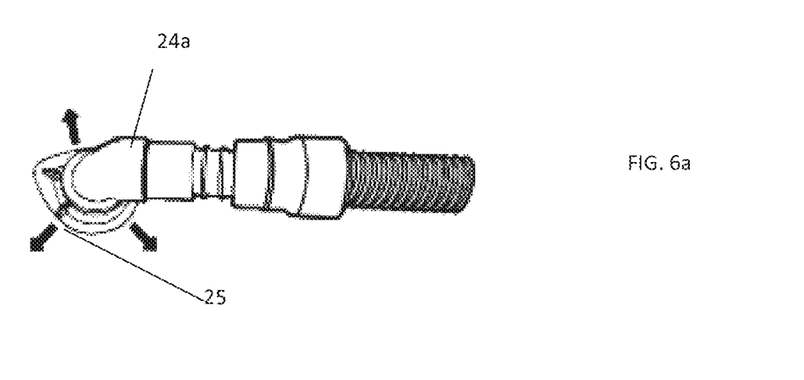
FIG. 6a, FIG. 6b and FIG. 6c show different angled connections for the patient interface.
Figure 6B:
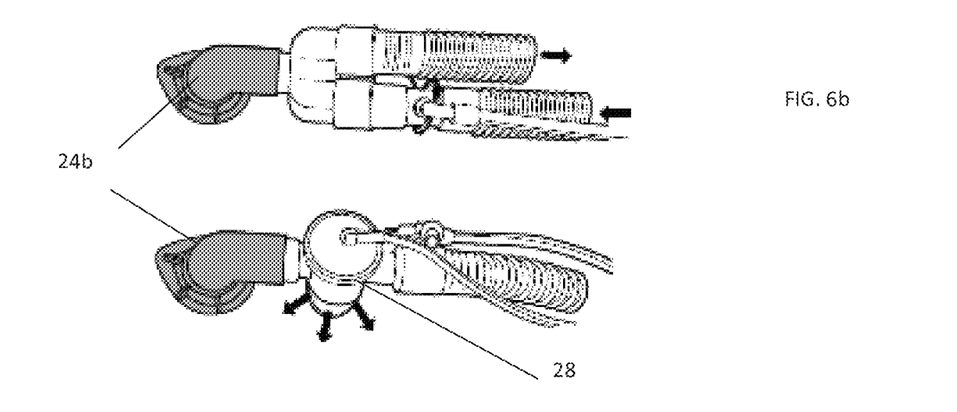
Figure 6C:
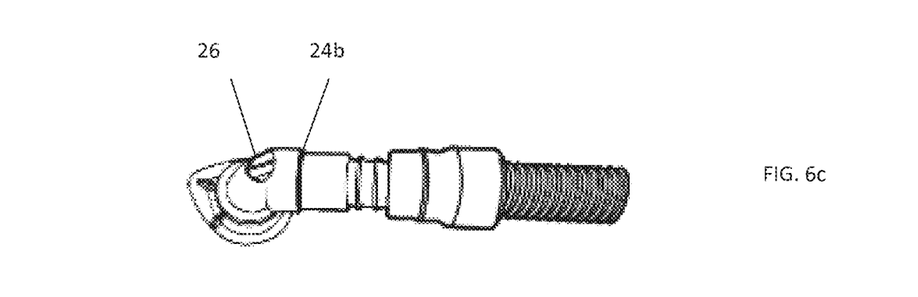

In FIG. 6a to FIG. 6c: at least 2, preferably at least 3, different, interchangeable angled connections (24a, b, c) are supplied for the patient interface.

Between the securing ring and the body of the patient interface or in the angled connection, the so-called vented angled connection (24a) has exhalation ports (25) via which breathing gas can be flushed out continuously. The exhalation ports may be designed in the form of a recess in the securing ring or in the form of a spacer element on the securing ring or in the form of a recess or in the form of a spacer element in the body of the patient interface. The vented angled connection is suitable, in particular, for connecting to a single-tube breathing system.

The so-called non-vented angled connection (24b) has no exhalation ports via which breathing gas is flushed out continuously. The non-vented angled connection is suitable, in particular, for connecting to a single-tube breathing system with an expiratory valve (28) in the vicinity of the patient. The non-vented angled connection is also suitable for connecting to a double-tube system with separate inspiration and expiration and an apparatus-mounted expiratory valve (28).

The non-vented angled connection is also suitable for connecting to a single-tube system with a separate exhalation valve.

The non-vented angled connection is additionally suitable for connecting to a single-tube system with a separate exhalation system and, as an additional safeguard in the event of the apparatus failing, an anti-asphyxia valve (AAV) (26).

The angled connection (24b) with an anti-asphyxia valve (AAV) (26) has, for this purpose, an atmospheric-air port, at least part of which can be closed from the inside by a membrane. For example, the angled connection has a membrane opening, for accommodating the membrane in the angled connection.

The atmospheric-air port allows unobstructed supply and discharge of the air during breaks in therapy. The membrane is inserted into the angled connection such that the membrane closes the atmospheric-air port during normal therapy operation as a result of the therapy pressure applied. The therapy operation here deflects the membrane out of its starting position. In the event of a drop in pressure, the membrane swings back into its starting position. The membrane thus closes in the direction of the tube, at least in part, and therefore prevents the patient from rebreathing into the breathing tube. The patient can then breathe ambient air via the atmospheric-air port.

Figure 7:
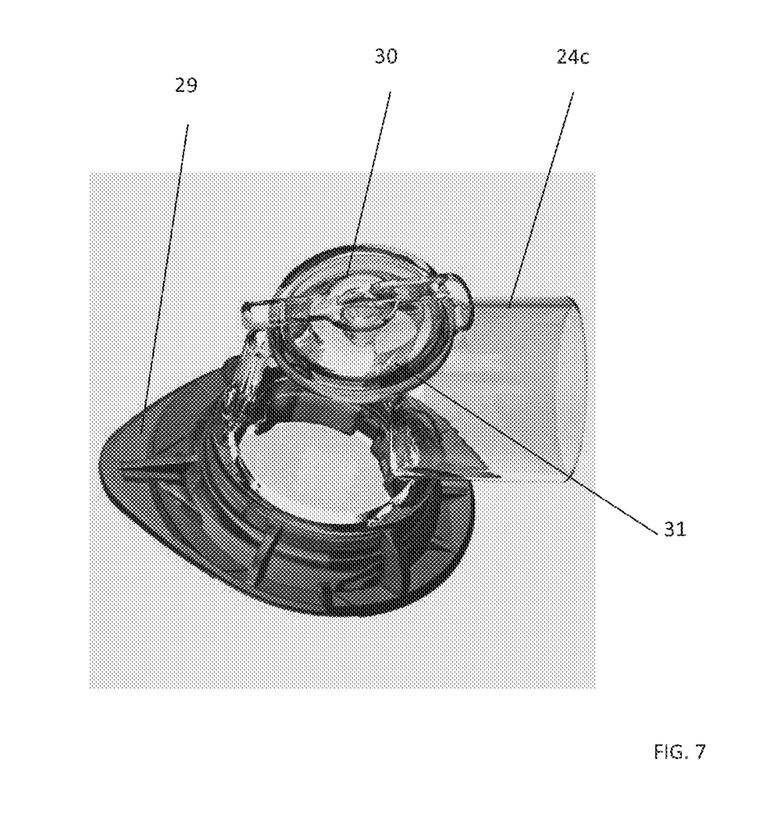
FIG. 7 shows an angled connection designed in the form of an endoscope adapter.

In FIG. 7: the angled connection, in addition, is also designed in the form of an endoscope adapter (24c) and allows for a bronchoscopy to be carried out without the patient's breathing having to be interrupted.

The endoscope adapter comprises a securing ring (29), which is not vented, and an angled connection which has a reclosable opening (30) for the endoscope. The endoscope adapter thus allows the doctor to carry out an endoscopy while the patient remains breathing throughout.

The endoscope adapter has an opening which can be closed by a preferably elastic closure cap (31). The closure cap likewise has an opening, which can be closed by a stopper. An endoscope is guided preferably through the opening in the elastic closure cap. The opening in the elastic closure cap here is dimensioned such that conventional endoscopes can be readily inserted, wherein the opening essentially abuts the endoscope, and therefore leakages are reduced. An optional lug secures the closure cap on the angled connection via a securing hook. The endoscope adapter allows for an endoscope to be inserted through the opening.

What is claimed is:

1. A spring arrangement, wherein the spring arrangement is capable of elastically supporting a patient interface on a patient and comprises a spring body having a base structure connectable to the patient interface via one or more connecting elements, wherein, starting from the base structure, inner walls and outer walls are arranged in an inclined state in relation to an axis extending in a spring direction and, at least in part, form a honeycomb structure, the outer walls of the spring body forming at least two knees, of which one knee is oriented radially outward and one knee is oriented inward, and further comprising a bearing surface, at least part of which extends parallel to the base structure, the bearing surface being spaced apart from the base structure in the spring direction by at least two honeycomb structures.

2. The spring arrangement of claim 1, wherein the inner and outer walls and/or the honeycomb structures terminate at a central structure, as seen in the spring direction, with a contact location.

3. The spring arrangement of claim 2, wherein a wall thickness of the contact location is reduced.

4. The spring arrangement of claim 2, wherein, from the central structure, inner walls and outer walls extend in an inclined state in relation to the spring direction and open out, by way of the contact location, in the bearing surface, at least part of which extends parallel to the base structure.

5. The spring arrangement of claim 4, wherein at least part of the bearing surface extends parallel to the base structure and parallel to the central structure.

6. The spring arrangement of claim 4, wherein inner and outer walls together with the bearing surface form the honeycomb structure.

7. The spring arrangement of claim 2, wherein a wall thickness of the contact location is thinner than that of the inner and/or outer walls.

8. The spring arrangement of claim 1, wherein inner and/or outer wall thicknesses are from about 1.2 mm to about 3.2 mm.

9. The spring arrangement of claim 1, wherein a thickness of the inner and/or outer walls and/or a material thickness of the honeycomb structure and/or a geometry of the honeycomb structure varies in the spring direction.

10. The spring arrangement of claim 1, wherein a spring displacement over a first stage is about 6 mm.

11. The spring arrangement of claim 1, wherein a spring displacement over a second stage is about 5 mm.

12. The spring arrangement of claim 1, wherein a spring constant overall ranges from about 0.26 to about 0.46 N/mm.

13. The spring arrangement of claim 1, wherein a height of the spring arrangement in the spring direction is about 25-35 mm.

14. A spring arrangement, wherein the spring arrangement is capable of elastically supporting a patient interface on a patient and comprises a spring body having a base structure connectable to the patient interface via one or more connecting elements, wherein, starting from the base structure, inner walls and outer walls are arranged in an inclined state in relation to an axis extending in a spring direction and at least in part, form a honeycomb structure, and further comprising a bearing surface, at least part of which extends parallel to the base structure, the bearing surface being spaced apart from the base structure in the spring direction by at least two honeycomb structures, and wherein the inner and outer walls and/or the honeycomb structures terminate at a central structure, as seen in the spring direction, with a contact location, and from the central structure, inner walls and outer walls extend in an inclined state in relation to the spring direction and open out, by way of the contact location, in the bearing surface.

15. The spring arrangement of claim 14, wherein the outer walls of the spring body form at least one knee.

16. The spring arrangement of claim 15, wherein the at least one knee is oriented radially outward.

17. The spring arrangement of claim 15, wherein the outer walls can be collapsed elastically in each case at the at least one knee.

18. The spring arrangement of claim 14, wherein a wall thickness of the contact location is reduced.

19. The spring arrangement of claim 14, wherein at least part of the bearing surface extends parallel to the central structure.

20. The spring arrangement of claim 14, wherein inner and outer walls together with the bearing surface form the honeycomb structure.

21. The spring arrangement of claim 14, wherein inner and/or outer wall thicknesses are from about 1.2 mm to about 3.2 mm.

22. The spring arrangement of claim 14, wherein a thickness of the inner and/or outer walls and/or a material thickness of the honeycomb structure and/or a geometry of the honeycomb structure varies in the spring direction.

23. The spring arrangement of claim 14, wherein a spring displacement over a first stage is about 6 mm and/or a spring displacement over a second stage is about 5 mm.

24. The spring arrangement of claim 14, wherein a spring constant overall ranges from about 0.26 to about 0.46 N/mm.

* * * * *